United States Patent [19]

Cherian

[11] Patent Number: 5,061,240
[45] Date of Patent: Oct. 29, 1991

[54] BALLOON TIP CATHETER FOR VENOUS VALVE ABLATION

[76] Inventor: George Cherian, 5136 W. 60th Ter., Mission, Kans. 66205

[21] Appl. No.: 502,700

[22] Filed: Apr. 2, 1990

[51] Int. Cl.$^5$ ............................................. A61M 29/00
[52] U.S. Cl. ........................................ 604/96; 604/98; 606/159; 606/194
[58] Field of Search ..................................... 604/96-99, 604/104-106, 22; 606/191, 192, 194, 159, 167, 170, 171

[56] References Cited

U.S. PATENT DOCUMENTS

| | | | |
|---|---|---|---|
| 3,837,345 | 9/1974 | Mator | 606/167 |
| 3,884,242 | 5/1975 | Bazell et al. | 604/96 |
| 4,351,341 | 9/1982 | Goldberg et al. | 604/96 |
| 4,493,321 | 1/1985 | Leather | 606/167 |
| 4,689,041 | 8/1987 | Corday et al. | 604/96 |
| 4,794,928 | 1/1989 | Kletschka | 606/194 |
| 4,832,691 | 5/1989 | Witzel | 604/96 |
| 4,952,215 | 8/1990 | Guriel et al. | 606/159 |

FOREIGN PATENT DOCUMENTS 2232334  1/1975  France .

Primary Examiner—C. Fred Rosenbaum
Assistant Examiner—Chalin Smith
Attorney, Agent, or Firm—Kokjer, Kircher, Bowman & Johnson

[57] ABSTRACT

A balloon tip catheter for tearing away one way valves in a vein so that the vein can be used as a bypass conduit without the valves dictating the venous flow direction. The catheter balloon has an arrowhead shape when inflated, with an annular groove formed in the arrowhead base adjacent to and extending around the catheter tube. When the balloon is pulled against the valve, the groove receives the valve flap and tears it away from the vein wall.

8 Claims, 1 Drawing Sheet

BALLOON TIP CATHETER FOR VENOUS VALVE ABLATION

BACKGROUND AND SUMMARY OF THE INVENTION

This invention relates generally to balloon tip catheters and more particularly to a catheter in which the balloon is specially constructed for use in the destruction of venous valve.

Veins have long been used by vascular surgeons to serve as vascular conduits to bypass blocked or clogged arteries. For example, the saphenous vein is commonly used to bypass various arteries that are plagued by blockage, including clogged leg arteries and coronary arteries. When the saphenous vein is used in leg surgery, in situ procedures are generally preferred because they allow the vein to remain in place without having to be removed and implanted at a new location. As can easily be appreciated, this minimizes damage to the tissue and increases the chances that the vein will function successfully to bypass the clogged part of the artery.

However, using the saphenous vein for in situ bypass procedures is not always possible. One major problem is that the veins are equipped with one way check valves that allow blood to flow in only one direction through the vein. If the flow direction in the artery that is to be bypassed is opposite the direction of flow allowed in the vein, it is necessary to remove the vein and turn it end for end before it can be attached to the artery as a bypass conduit. Thus, the vein cannot remain in place and the advantages of the in situ procedure are lost.

The presence of the venous valves also creates problems in other types of operations. For example, when the saphenous vein is used in coronary bypass surgery or other bypass surgery, it can only be oriented in one way because of the valves, and this prevents the vein from being reversed in situations where reversal of its orientation is otherwise desirable.

It is the principal goal of the present invention to provide a catheter which can be used to destroy venous valves without damaging the lining or wall of the vein so that the vein can be used in bypass surgery without regard to directional limitations. Although the invention is especially well-suited for in situ surgical procedures, it is desirable in many other types of surgery for the venous valves to be removed, and the invention thus finds use in a wide variety of surgical applications.

In accordance with the invention, a balloon tip catheter is equipped with a specially shaped balloon having an arrowhead shape. The base of the arrowhead presents an annular groove extending around the catheter tube so that the balloon can be moved past the valve in a deflated position, inflated to the arrowhead shape, and then pulled back so that the lip or edge of the valve is received in the groove of the balloon. Further pulling of the catheter causes the balloon to tear the valve away from the wall of the vein so that the vein can thereafter be used in an in situ procedure or removed and implanted elsewhere without regard to its orientation.

Other and further objects of the invention, together with the features of novelty appurtenant thereto, will appear in the course of the following description.

DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE INVENTION

Figure 1:
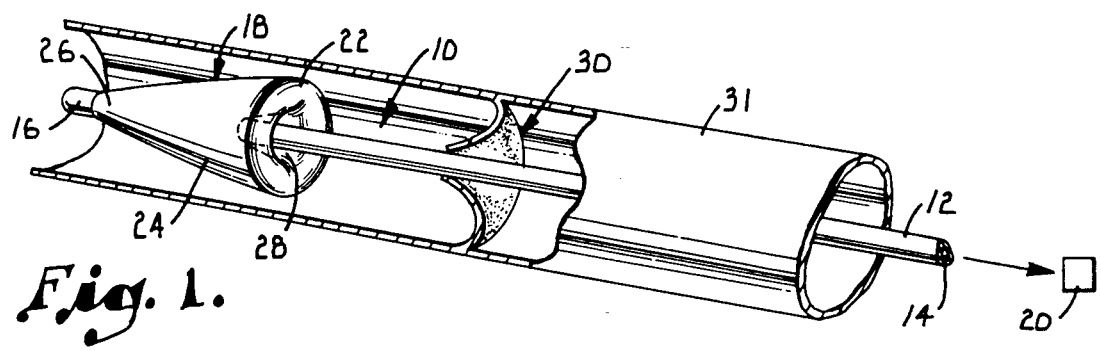
FIG. 1 is a fragmentary perspective view of a balloon tip catheter constructed in accordance with the present invention applied to a vein in order to tear away a one-way valve in the vein, with the balloon shown in the inflated condition.

Referring now to the drawings in more detail, numeral 10 designates a balloon tip catheter constructed in accordance with a preferred embodiment of the present invention. The catheter 10 includes an elongated catheter tube 12 which is preferably constructed of a plastic material of the type commonly used in the construction of catheters. A longitudinal fluid passage 14 extends the entire length of the catheter tube 12. The catheter tube 12 has a tip end 16 which is equipped with an inflatable balloon generally identified by numeral 18. On the opposite end, the catheter tube 12 is equipped with a syringe fitting 20 (FIG. 1) for receiving a syringe or other instrument (not shown) used to inject fluid (normally a saline solution) through the passage 14 to the balloon 18. The tip 16 is preferably constructed of a soft and pliable substance to avoid damaging the delicate veins during use of the catheter.

Figure 2:
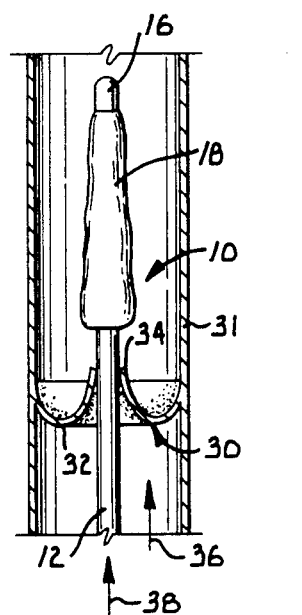
FIG. 2 is a fragmentary sectional view through the vein and showing the balloon being passed through the valve in a deflated condition.

The balloon 18 has a deflated condition shown in FIG. 2 in which the balloon is generally collapsed around the catheter tube 12. In the inflated condition shown in FIGS. 1 and 3-4, the balloon 18 is shaped generally in the configuration of an arrowhead. A base portion 22 of the arrowhead gradually curves from the catheter tube 12 in a direction outwardly and away from the tip end 16 of the catheter. The arrowhead also has a body portion 24 which gradually and uniformly tapers from the base 22 toward the tip end of the catheter. The arrowhead terminates in a pointed end 26 located adjacent to the tip 16. The base 22 presents a generally annular groove 28 which extends around the catheter tube 12 at a location adjacent to it. The balloon 18 is symmetrical about the axis of the catheter tube 12.

The catheter 10 is used for the venous ablation of one way check valves such as the valve which is generally identified by numeral 30 and which is formed in a vein 31. The valve 30 takes the form of a flap 32 which is secured to the wall of the vein 31 around its periphery and which terminates in a free circular edge 34 located near the center of the vein 31. Typically, the vein 31 will have a number of one way valves 30 spaced apart from one another. The valves allow blood flow in the direction indicated by the directional arrow 36 in FIG. 2. Because of the curvature of the flap 32, the blood is able to flow in the direction 36 through the aperture defined within the edge 34. However, flow in the opposite direction is precluded because the pressure of the blood closes the aperture within the edge 34 and prevents blood from passing through the valve.

Figure 3:
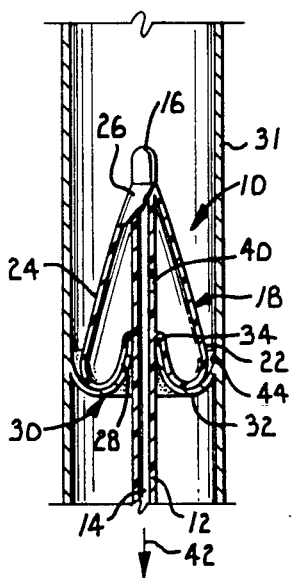
FIG. 3 is a fragmentary sectional view similar to FIG. 2, but showing the balloon in the inflated condition after having been passed through the valve and pulled back against it.

In use of the catheter 10, the catheter tip 16 is inserted into the vein 31, and, with the balloon 18 in the deflated condition, the catheter tube is extended into the vein in the direction indicated by the directional arrow 38 in FIG. 2. Because the balloon 18 is able to pass through the aperture within edge 34 in the deflated condition, the tip 16 and balloon 18 can be extended past the valve 30. Then, the balloon 18 is inflated by injecting fluid under pressure through the fitting 20 and the passage 14. As best shown in FIG. 3, the catheter tube 12 is provided with a port 40 which opens inside of the balloon 18, and the fluid is thus able to enter the balloon and inflate it to the inflated condition.

After the balloon has been inflated, the catheter tube 12 is pulled in the direction indicated by the directional arrow 42 in FIG. 3 in order to bring the base 22 against the valve flap 32. The curvature of the base 22 generally conforms with the curvature of the valve flap 32, and the edge 34 of the valve flap is received in the annular groove 28 in the base of the balloon. The valve flap is thus gripped in the groove 28, and further pulling of the catheter tube 12 in the direction indicated by arrow 42 causes the balloon 18 to tear the valve flap 32 away from the wall of the vein 31.

Figure 4:
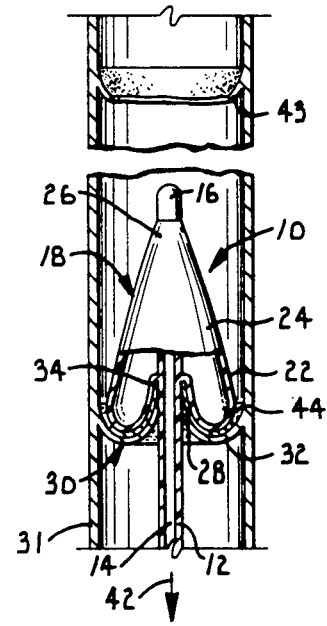
FIG. 4 is a fragmentary sectional view similar to FIG. 3 and showing the balloon in an inflated condition after having torn away one venous valve and in position to tear away another valve.

Normally, the catheter balloon 18 will initially be extended through all of the valves 30 that are to be destroyed and then pulled in the opposite direction in order to destroy the valves one after the other until all of the valves have been torn away. This is best illustrated in FIG. 4 which shows only a remnant 43 of a valve that has been destroyed and the balloon 18 in position to destroy another valve upon further movement in the direction 42.

The maximum diameter of the arrowhead shaped balloon 18 in the inflated condition is at the base 22, and it is preferred for a small clearance 44 (see FIGS. 3 and 4) to be provided between the base 22 and the lining of the vein 31. Preferably, the clearance distance 44 is no more than about one millimeter.

It is contemplated that the balloon 18 will be provided in at least three different sizes (such as with a three millimeter maximum base diameter, a four millimeter maximum base diameter and a five millimeter maximum based diameter). This can be accomplished either by providing three different sized balloons 18 or by providing a single balloon that can be inflated to three different sizes depending upon the amount of fluid that is injected to inflate the balloon. Larger or smaller sizes can also be made as required.

The arrowhead shape of the balloon 18 is important in permitting the catheter to effectively and efficiently remove venous valves 30. The provision of the groove 28 allows the balloon 18 to receive and grip the free edge portion 34 of the valve flap in order to tear the valve away from the wall of the vein. The shape of the base 22 conforms generally with the configuration of the valve flap 32 and also provides a single line of maximum diameter of the inflated balloon. Consequently, at most, the balloon will have single line contact with the lining of the vein 31, thus minimizing the chance of injuring the vein lining. The gradual taper of the body 24 toward the pointed end 26 prevents the tip end of the catheter from contacting and possibly damaging the lining of the vein.

The groove 28 should have a depth in the range of approximately 2-5 millimeters and it has been found that a three millimeter groove depth is desirable in most applications. If the groove is too deep, the edge 34 does not bottom out in the groove. Conversely, if the groove is too shallow, the edge 34 bottoms out before the base 22 is positioned adjacent the majority of the flap 32.

Figure 5:
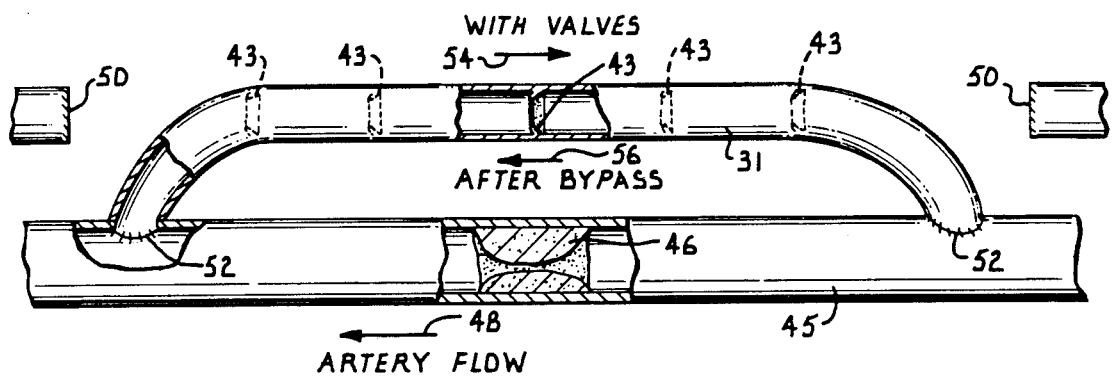
FIG. 5 is a fragmentary elevational view showing the vein connected to bypass blockage in an artery with all of the valves in the vein having been destroyed by the catheter.

FIG. 5 illustrates a typical surgical application of the catheter 10. An artery 45 has a blockage 46 which impedes flow of blood in the direction indicated by the arrow 48 which is the direction of blood flow through the artery. The vein 31 is initially located near and to one side of the artery 45 and is used during an in situ surgical procedure to bypass the blockage 46. In carrying out the in situ procedure, the catheter 10 is first used to destroy all of the valves in the portion of the vein 31 that is to be used in the bypass, thus leaving only the valve remnants 43 in the vein 31. The portion of the vein which is to be used in the bypass is cut away from the rest of the vein at locations on opposite sides of the blockage 46, and sutures 50 are used to close the portions of the vein on opposite sides of the cuts. The vein 31 is then sutured to the artery 45 on opposite sides of the blockage 46, as indicated at 52.

It is noted that with the valves in place in the vein 31, blood is able to flow through the vein only in the direction indicated by the directional arrow 54 which is opposite the direction 48 in which blood flow takes place through the artery 45. However, with the valves removed and only the remnants 43 remaining, blood can flow through the vein 31 in the direction indicated by the directional arrow 56 which is the same direction as the flow through the artery 45. Because the vein 31 can remain in its original place except for the end portions which are cut and attached to the artery 45, the in situ bypass minimizes damage to the tissue and the chances are thus improved that the vein 31 will be able to serve as an effective bypass for the blockage 46.

Although the catheter 10 of the present invention is particularly useful in carrying out in situ bypass procedures, it is to be understood that it is also useful in other surgical applications in which destruction of venous valves is necessary or desirable.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A catheter for use in the venous ablation of a one way vascular valve located in a vein and having a curved valve flap terminating in a generally circular edge, said catheter comprising:

a catheter tube having a tip end and a fluid passage extending through the tube to the tip end; and a soft and pliable balloon on said tip end of the catheter having deflated and inflated conditions and communicating with said fluid passage to receive fluid therefrom for inflation, said balloon having in the inflated condition thereof a shape presenting a curved base applicable to the valve flap and having a size and shape to fit against the valve flap in conformity therewith, said balloon having in the inflated condition an annular groove in the base sized and located to closely receive said edge therein when the base is applied to the valve flap and to grip said edge in a manner to tear the vale flap when the balloon is moved past the flap in the deflated condition and then inflated and pulled toward the flap with said groove closely receiving the edge therein, said base being smaller than the vein to present a clearance space within the vein around said base.

2. The catheter of claim 1, wherein said annular groove is located adjacent to and extends around the catheter tube.

3. The catheter of claim 2, wherein said balloon has in the inflated condition a body portion which tapers away from said base toward the tip end of the catheter tube.

4. The catheter of claim 1, wherein said balloon has in the inflated condition a body portion which tapers away from said base toward the tip end of the catheter tube.

5. A catheter for use in a vein having a one way valve flap which curves inwardly from a wall of the vein toward a free edge of the flap, said catheter comprising:

a catheter tube having a diameter smaller than the vein and terminating in a tip end, said catheter tube presenting a fluid passage extending to said tip end; and a soft and pliable balloon on said tip end of the catheter having inflated and deflated conditions and communicating with the fluid passage to receive fluid therefrom for inflation of the balloon, said balloon having in the inflated condition thereof an arrowhead shape with an arrowhead base presenting an annular groove around the catheter tube sized and located to closely receive the edge of the flap and with an arrowhead body gradually tapering from the base toward the tip end of the catheter tube, said balloon being able to pass the valve flap in the deflated condition and being thereafter inflatable to permit the free edge of the valve flap to be closely received in said groove and gripped therein in a manner to tear the valve flap when the catheter is pulled past the flap location in the inflated condition of the balloon, said base being smaller than the vein to present a clearance space between the base and the wall of the vein when said base is applied to the valve flap.

6. The catheter of claim 5, wherein said groove is adjacent the catheter tube.

7. In a balloon tip catheter having a catheter tube presenting a fluid passage and an inflatable balloon on the catheter tube, the improvement wherein the balloon has a shape when inflated to present a curved base sized and shaped for application to a one way venous valve flap and a body which gradually tapers at a point away from said base, said base presenting therein an annular groove sized and located to closely receive and grip an edge of the valve flap in a manner to tear the valve flap when the catheter is pulled with the valve flap edge received in said groove, said base being smaller in an inflated condition of the balloon than a vein containing the valve flap to provide a clearance space in the vein around the base.

8. The improvement of claim 7, wherein said groove has a depth in the range of approximately 2-5 millimeters.

* * * * *